United States Patent
Hung et al.

(10) Patent No.: US 8,623,339 B2
(45) Date of Patent: Jan. 7, 2014

(54) HAIR BLEACHING COMPOSITION AND METHOD FOR PRODUCING SAME

(75) Inventors: Kar Yan Hung, Hong Kong (HK); Ka Yee Ho, Hong Kong (HK)

(73) Assignee: Artec Chemical Company Limited, Hong Kong (HK)

( * ) Notice: Subject to any disclaimer, the term of this patent is extended or adjusted under 35 U.S.C. 154(b) by 0 days.

(21) Appl. No.: 13/425,374

(22) Filed: Mar. 20, 2012

(65) Prior Publication Data

US 2013/0251768 A1 Sep. 26, 2013

(51) Int. Cl.
- *A61K 8/00* (2006.01)
- *A61K 8/02* (2006.01)
- *A61K 9/14* (2006.01)
- *A61Q 5/08* (2006.01)

(52) U.S. Cl.
USPC ............... 424/62; 424/401; 424/489; 424/69

(58) Field of Classification Search
USPC ..................... 424/401, 62, 489, 69
See application file for complete search history.

(56) References Cited

U.S. PATENT DOCUMENTS 5,989,530 A * 11/1999 Lorenz et al. ............. 424/62
2006/0286048 A1 * 12/2006 Morrison et al. .......... 424/63

* cited by examiner

*Primary Examiner* — Rachael E Bredefeld

(57) ABSTRACT

A bleaching composition includes at least a powder ingredient that is capable of retaining oil on its surface, at least a powdery carrier material, and 0.5% to 2.5% by weight of oil. The bleaching composition is in a form of agglomerated particles that are free-flowing and dust free. A method for producing the bleaching composition is also provided.

9 Claims, 2 Drawing Sheets

HAIR BLEACHING COMPOSITION AND METHOD FOR PRODUCING SAME

FIELD OF THE PATENT APPLICATION

The present patent application generally relates to hair bleaching compositions and more specifically to a human hair bleaching composition that is free-flowing and dust free, and to a method for producing the same.

BACKGROUND

Traditional powdery human hair bleaching composition generally includes solid peroxide and some pulverulent particles. The pulverulent particles can be alkaline agent, thickeners, or surfactants. Most commonly, particles such as, alkaline silicate, silicon dioxide, alkaline stearate and alkaline carbonate are used. These ingredients are commonly used as dry powders which must be mixed with aqueous solution or emulsion of hydrogen peroxide before they are applied to hair for coloring. During handling and mixing, fine dusts are generated by the collision and abrasion of powders with each other. The fine dusts of persulfate compounds and alkaline silicate can irritate human eyes, respiratory canals and mucous membranes. More and more research has been done to investigate the association between asthma and exposure to hair bleaches among hairdressers.

To overcome such disadvantages, several patents have disclosed various compositions and methods to make dust free bleaching powder. U.S. Pat. No. 4,170,637 discloses hair bleaching compositions that include an intimate mixture of at least one particulate persulfate salt and at least one alkali silicate with 30%-70% by weight of an anhydrous organic carrier base of the total mixture. These compositions are not free-flowing powders, but instead as paste or cream, they are much more difficult to manufacture and pack for use.

In general, various oil and wax can be used to produce dustless bleaching compositions as long as it will not affect the bleaching and dissolving properties of the bleaching composition during application. U.S. Pat. No. 5,891,423 discloses the treatment of dust-forming bleaching powder with about 10% to 25% by weight of the inert oil, while the preferred range is from about 14% to 20% by weight to the total composition. U.S. Pat. No. 5,989,530 discloses another type of hair bleaching composition that includes at least one solid peroxide compound, at least one powdery carrier material, and about 2.5% to 25% by weight of oil and/or liquid wax, while the most preferred range is around 8% to 12% by weight of the total composition. U.S. Pat. No. 5,866,107 discloses the testing results of poor thixotropy property of prior art commercial products when 10% by weight of mineral oil is added to the bleaching compositions. Extra embrocation or wetting is then required to make the hair bleaching more effective and even due to the poor thixotropy. The unstable oil emulsion is formed during mixing of the water insoluble oil and/or wax with the aqueous solution of hydrogen peroxide. It takes a longer time for the paste to become in a stable form. At the same time, the oil and/or wax residues remain on the hair after application, which is difficult to wash off. Therefore, the use of oil and/or wax should be minimized in the production of the dust free bleaching powders.

The amount of oil for producing dust free bleaching compositions depends on many parameters such as the properties of the oil, the oil adsorption property of powder ingredients in the bleaching compositions and the process for mixing the oil into the bleaching compositions. The oil should be a liquid with a low viscosity at a temperature below 30 degrees so that it can be easily sprayed into the powder ingredients in the bleaching composition. The use of powder ingredients with high extent of oil adsorption property should be avoided as excess oil may be adsorbed on the internal surface area of the powder ingredients. The excess oil may be released out during mixing with the hydrogen peroxide solution in the hair bleaching application.

SUMMARY

The present patent application is directed to a bleaching composition. In one aspect, the bleaching composition includes at least a powder ingredient that is capable of retaining oil on its surface, at least a powdery carrier material, and 0.5% to 2.5% by weight of oil. The bleaching composition is in a form of agglomerated particles that are free-flowing and dust free.

The agglomerated particles may be retainable on a 300 mesh sieve. The powder ingredient may be present by weight from 25% to 65%. The powder ingredient may be selected from the group consisting of potassium persulfate, ammonium persulfate, sodium persulfate, urea peroxide, melamine peroxide, strontium peroxide, magnesium peroxide, sodium metasilicate, and ammonium chloride.

The oil may be inert with respect to the other ingredients of the beaching composition, and selected from the group consisting of minerals oil, silicone oil, hydrocarbons with ether linkages, hydrocarbon with polyethylene glycol chains, animal oil and vegetable oil. The oil may have a viscosity in the range of 5 mm$^2$/s to 350 mm$^2$/s.

In another aspect, the present patent application provides a method for producing a bleaching composition. The method includes spraying oil on at least a powder ingredient that is capable of retaining oil on the surface thereof; mixing the powder ingredient with at least a powdery carrier material; and stirring the mixture at a speed of 20 to 50 rotations per minute for 5 to 30 minutes.

The oil may be present in the mixture by weight from 0.5% to 2.5%. The oil may be inert with respect to the other ingredients of the beaching composition, and selected from the group consisting of minerals oil, silicone oil, hydrocarbons with ether linkages, hydrocarbon with polyethylene glycol chains, animal oil and vegetable oil.

The method may further include forming agglomerated particles that is retainable on a 300 mesh sieve. When spraying the oil, the powder ingredient may be continuously stirred at a speed of 20 to 50 rotations per minute.

The mixture may be stirred for 15 to 20 minutes. The powder ingredient may be present in the mixture by weight from 25% to 65%. The powder ingredient may be selected from the group consisting of potassium persulfate, ammonium persulfate, sodium persulfate, urea peroxide, melamine peroxide, strontium peroxide, magnesium peroxide, sodium metasilicate, and ammonium chloride. The oil may have a viscosity in the range of 5 mm$^2$/s to 350 mm$^2$/s.

In yet another aspect, the present patent application provides a bleaching composition including at least a powder ingredient that is capable of retaining oil on its surface, at least a powdery carrier material, and 0.5% to 2.5% by weight of oil. The bleaching composition is in a form of agglomerated particles that are retainable on a 300 mesh sieve. The powder ingredient is present by weight from 25% to 65%.

The oil may be present by weight from 1% to 2%. The powder ingredient may be present by weight from 35% to 50%. The oil may be mineral oil or silicone oil with a viscosity in the range of 7 mm$^2$/s to 120 mm$^2$/s. The powder ingredient may be selected from the group consisting of potassium persulfate, ammonium persulfate, sodium persulfate, urea peroxide, melamine peroxide, strontium peroxide, magnesium peroxide, sodium metasilicate, and ammonium chloride.

BRIEF DESCRIPTIONS OF THE DRAWINGS

DETAILED DESCRIPTION

Figure 1:
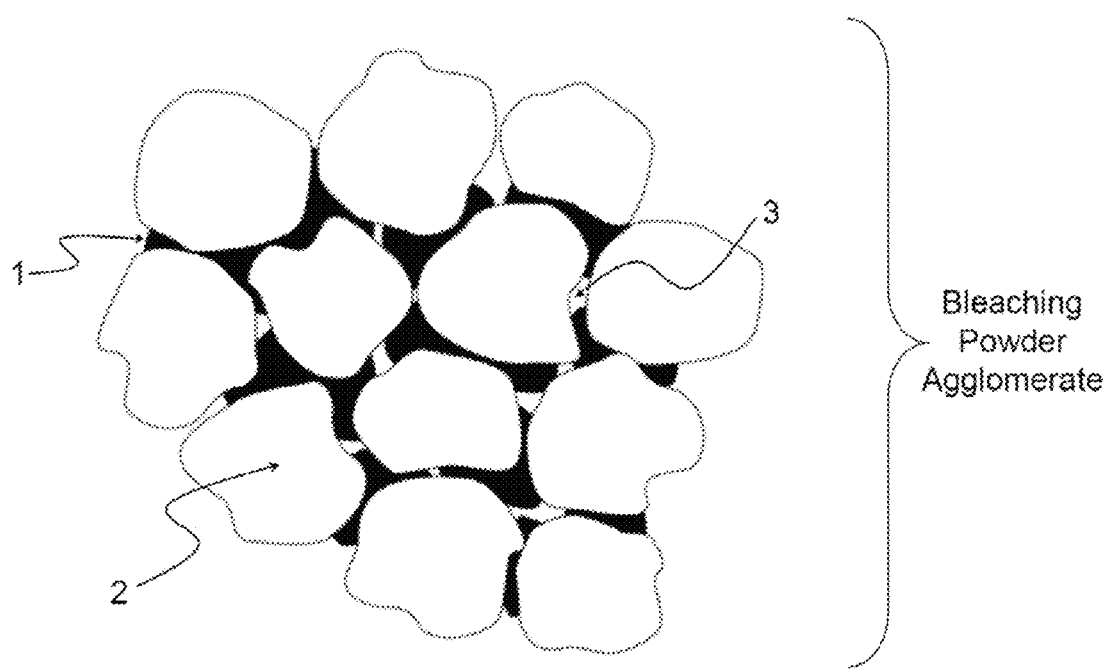
FIG. 1 is a microscopic view of the bleaching powder agglomerate according to an embodiment of the present patent application.

Reference will now be made in detail to a preferred embodiment of the hair bleaching composition and the method for producing the same disclosed in the present patent application, examples of which are also provided in the following description. Exemplary embodiments of the hair bleaching composition and the method for producing the same disclosed in the present patent application are described in detail, although it will be apparent to those skilled in the relevant art that some features that are not particularly important to an understanding of the hair bleaching composition and the method for producing the same may not be shown for the sake of clarity.

Furthermore, it should be understood that the hair bleaching composition and the method for producing the same disclosed in the present patent application is not limited to the precise embodiments described below and that various changes and modifications thereof may be effected by one skilled in the art without departing from the spirit or scope of the protection. For example, elements and/or features of different illustrative embodiments may be combined with each other and/or substituted for each other within the scope of this disclosure.

According to an embodiment of the present patent application, a powdery hair bleaching composition includes of at least one powder ingredient that can retain oil on its surface, one powdery carrier material, and low viscosity oil which is preferable from about 1% to about 2% by weight of the said bleaching composition so that the bleaching composition is free-flowing and dust free, and can be retained on a 300 mesh sieve.

Suitable powder ingredients for use in the step of mixing with oil includes potassium persulfate, ammonium persulfate, sodium persulfate, urea peroxide, melamine peroxide, strontium peroxide, magnesium peroxide, sodium metasilicate, ammonium chloride and a mixture thereof. Preferred powder ingredients include sodium persulfate and ammonium chloride. The preferred amount of powder ingredients in the powdery bleaching composition is in the range of about 25% to about 65% by weight, more preferably about 35% to about 50% by weight.

The oil in the embodiment should not chemically affect the bleaching and dissolving properties of the bleaching composition during application. Therefore, the oil in this embodiment is inert with respect to the other ingredients of the powdery bleaching composition. Various synthetic and natural oils can be obtained commercially, for example from Dow Corning, Croda, Cognis, Lipo Chemicals, Sonneborn, Calumet Penreco, Eco Oil Argentina, Floratech Americas and etc. Suitable inert oil with a viscosity from about 5 $mm^2/s$ to about 350 $mm^2/s$ for use in the embodiment includes light grade cosmetics minerals oil, silicone oil, hydrocarbons with ether linkages, hydrocarbon with polyethylene glycol chains, animal or vegetable oil such as anhydrous lanolin oil, jojoba oil, and olive oil. Preferred oil includes mineral oil and silicone oil with a viscosity from about 7 $mm^2/s$ to about 120 $mm^2/s$. The amount of oil in the powdery bleaching composition is in the range of about 0.5% to about 2.5% by weight, more preferably about 1% to about 2% by weight of the powdery bleaching composition.

The production of the bleaching composition can be conducted by spraying the inert oil under pressure on at least one powder ingredient that is capable of retaining the oil on its surface. During spraying, the powder ingredient is continuously stirred at a speed of around 20 to 50 rotations per minute. Then the powder ingredient is mixed with other components of the bleaching composition and continuously stirred at around 20 to 50 rotations per minute for about 5 minutes to about 30 minutes, preferably for about 15 to about 20 minutes. This can ensure a good dispersion of the oil coated powder ingredient among other components so that agglomerated particles that is retainable on a 300 mesh sieve is formed.

FIG. 1 is a microscopic view of the bleaching powder agglomerate. Referring to FIG. 1, the oil 1 acts as liquid bridges among the small particles 2 inside the bleaching composition. Air spaces 3 are found among the small particles 2 after the dust free bleaching powder agglomerates are obtained. All the bleaching powder agglomerates can be retained on a 300 mesh sieve.

The following two examples further illustrate the effect of including inert oil in the bleaching composition in terms of producing agglomerated bleaching particles.

Example 1

In one example, referring to Table 1, Formulation A and C are tested formulations that contain a mixture of persulfate with a pH controlling agent such as silicates. Other ingredients such as thickening agents and surfactant are also included. In Formulation A, 1.95% by weight of mineral oil to the bleaching composition is firstly sprayed on the sodium persulfate. The oil coated sodium persulfate is then mixed with other components with a stirring at around 35 rotations per minute for around 20 minutes to form groups of bigger agglomerated particles. Formulation B is commercially available for hair bleaching formulation. 2% by weight of silicone oil to the bleaching composition is sprayed on the potassium persulfate which is then mixed with other components of the bleaching composition under the same stirring rate and duration as Formulation A. Formulation C is prepared according to the U.S. Pat. No. 5,891,423. 1.3% by weight of isopropyl palmitate to the bleaching composition is sprayed on the ammonium chloride which is then mixed with other components of the bleaching composition under the same stirring rate and duration as Formulation A.

Table 1 clearly shows that the spraying of 1.3 to 2.0% of oil can effectively increase the percentage by weight of larger particles for all formulations and all powders that can be retained on a 300 mesh sieve.

TABLE 1

Sieve Analysis of Bleaching Powder Formulations (% by weight)

| Mesh Size | Particle Size (Microns) | Formulation A | Formulation A with Oil | Formulation B | Formulation B with Oil |
|---|---|---|---|---|---|
| 60 | >250 | 6.7 | 23.7 | 11.2 | 11.4 |
| 100 | >149 | 35.9 | 48.9 | 27.6 | 36.2 |
| 200 | >74 | 33.4 | 22.5 | 45.8 | 52.4 |

TABLE 1-continued

Sieve Analysis of Bleaching Powder Formulations (% by weight)

| 300 | >48 | 13.2 | 4.9 | 10.6 | 0 |
| 400 | >37 | 10.6 | 0 | 4.8 | 0 |
| *Pass 400 | <37 | 0.2 | 0 | 0 | 0 |

| Mesh Size | Particle Size (Microns) | Formulation C | Formulation C with Oil |
|---|---|---|---|
| 60 | >250 | 32.2 | 29.9 |
| 100 | >149 | 26.8 | 31.3 |
| 200 | >74 | 21.8 | 35.1 |
| 300 | >48 | 9.5 | 3.7 |
| 400 | >37 | 9.0 | 0 |
| *Pass 400 | <37 | 0.7 | 0 |

*Pass 400 means powders pass through 400 mess size sieve

Figure 2:
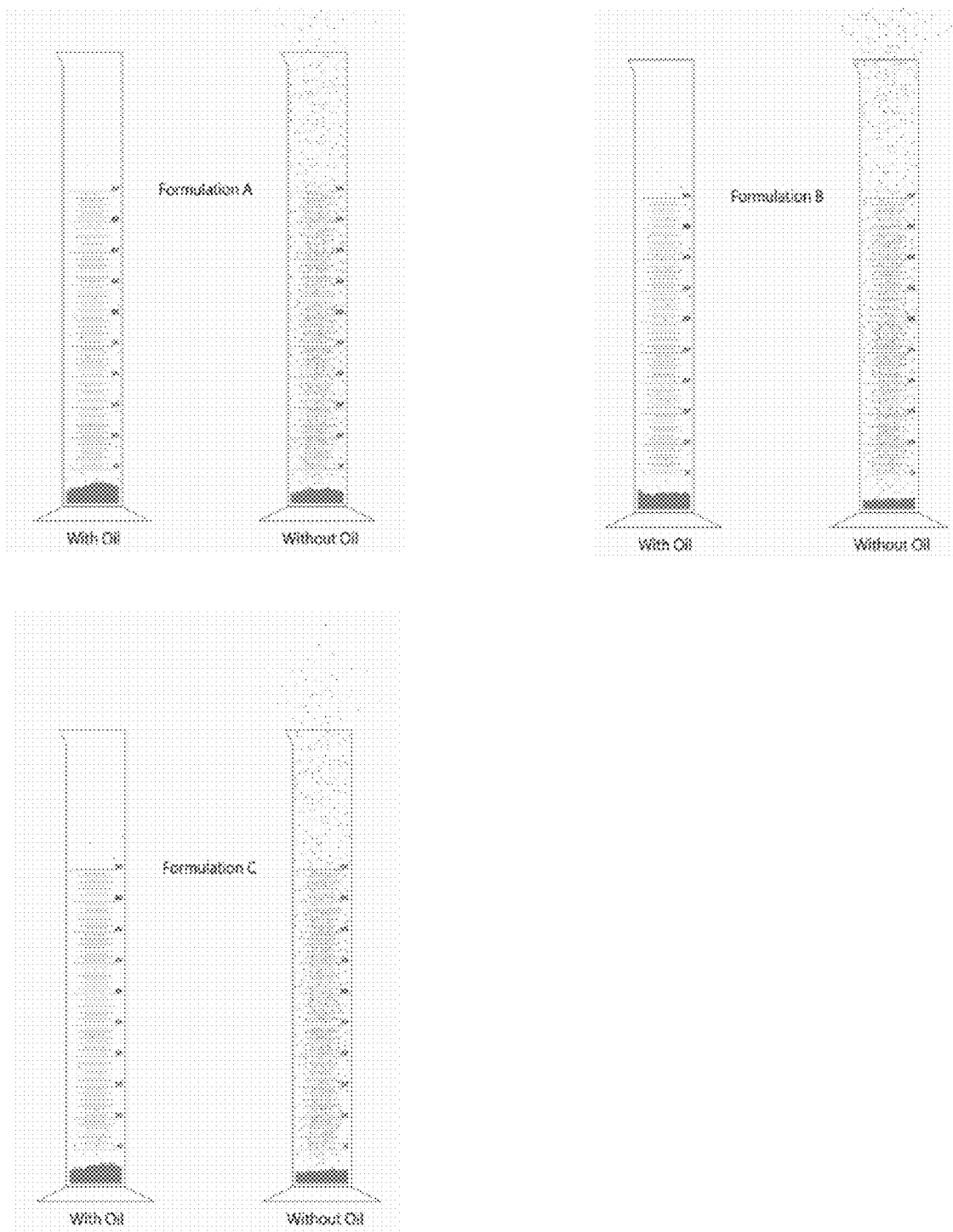
FIG. 2 is a pictorial representation of the dustiness testing results of three formulations according to an embodiment of the present patent application.

To assess the dustiness of a sample, 15 g of powder is poured from a round bottom spoon with a diameter of 4 cm to the top of a 500 ml measuring cylinder with a diameter of 5 cm and a height of 37.5 cm. FIG. 2 is a pictorial representation of the dustiness testing results of the above three formulations.

Without the oil as the liquid bridges for the formation of larger particles, dust can be observed over the top of the measuring cylinder for several minutes for all three formulations. However, no dust is observed over the top of the cylinders when oil is used as the liquid bridges for the formation of larger particles. Therefore, the spraying of 1 to 2% by weight of inert oil to the bleaching composition on at least one powder ingredient of the bleaching composition is effective to produce agglomerated bleaching particles that can be retained on a 300 mesh sieve.

Example 2

In another example, different percentages by weight (such as 1%, 1.5% and 2% by weight) of inert oil is added into Formulations A, B and C in order to study the particle sizes of these formulations with respective to the percentages by weight of the inert oil. For Formulation A, mineral oil is sprayed on the sodium persulfate. Then oil coated sodium persulfate is then mixed with other components with a stirring at around 35 rotations per minute for around 20 minutes to form groups of bigger agglomerated particles. For commercially available Formulation B, silicone oil is sprayed on the potassium persulfate which is then mixed with other components of the bleaching composition under the same stirring rate and duration as Formulation A. For Formulation C, isopropyl palmitate is sprayed on the ammonium chloride, which is then mixed with other components of the bleaching composition under the same stirring rate and duration as Formulation A. Table 2 clearly shows that 2% by weight of inert oil for all these formulations is effective to produce agglomerated bleaching particles that can be retained on a 300 mesh sieve.

TABLE 2

Sieve Analysis of Bleaching Powder Formulations (% by weight)

| Mesh Size | Particle Size (Microns) | Formulation A | Formulation A with 1% by weight of Oil | Formulation A with 1.5% by weight of Oil | Formulation A with 2% by weight of Oil |
|---|---|---|---|---|---|
| 60 | >250 | 6.7 | 6.4 | 9.9 | 8.6 |
| 100 | >149 | 35.9 | 40.8 | 50.4 | 58.8 |
| 200 | >74 | 33.4 | 44.3 | 37.8 | 32 |
| 300 | >48 | 13.2 | 8.2 | 1.9 | 0.6 |
| 400 | >37 | 10.6 | 0.3 | 0 | 0 |
| *Pass 400 | <37 | 0.2 | 0 | 0 | 0 |

| Mesh Size | Particle Size (Microns) | Formulation B | Formulation B with 1% by weight of Oil | Formulation B with 1.5% by weight of Oil | Formulation B with 2% by weight of Oil |
|---|---|---|---|---|---|
| 60 | >250 | 11.2 | 17.2 | 14.4 | 11.4 |
| 100 | >149 | 27.6 | 36.0 | 32.4 | 36.2 |
| 200 | >74 | 45.8 | 34.5 | 36.4 | 52.3 |
| 300 | >48 | 10.6 | 11.3 | 16.2 | 0.1 |
| 400 | >37 | 4.8 | 1.0 | 0.6 | 0 |
| *Pass 400 | <37 | 0 | 0 | 0 | 0 |

| Mesh Size | Particle Size (Microns) | Formulation C | Formulation C with 1% by weight of Oil | Formulation C with 1.5% by weight of Oil | Formulation C with 2% by weight of Oil |
|---|---|---|---|---|---|
| 60 | >250 | 32.2 | 38.8 | 41.5 | 38.9 |
| 100 | >149 | 26.8 | 34.9 | 38.5 | 37.9 |
| 200 | >74 | 21.8 | 24.1 | 19.2 | 22.2 |
| 300 | >48 | 9.5 | 2.2 | 0.8 | 1.0 |
| 400 | >37 | 9.7 | 0 | 0 | 0 |
| *Pass 400 | <37 | 0.7 | 0 | 0 | 0 |

In another embodiment, the application of the powdery bleaching composition can be conducted by mixing the powdery bleaching composition with a 6% to 12% by weight hydrogen peroxide solution. Preferably, 1 part of the powdery bleaching composition is mixed with 1.5 parts of a 9% by weight hydrogen peroxide solution, and thereafter applying the mixture to human hair for 30 minutes.

While the present patent application has been shown and described with particular references to a number of embodiments thereof, it should be noted that various other changes or modifications may be made without departing from the scope of the present invention.

What is claimed is:

1. A bleaching composition consisting of:
   at least a powder ingredient that is capable of retaining oil on its surface selected from the group consisting of potassium persulfate, ammonium persulfate, sodium persulfate, urea peroxide, melamine peroxide, strontium peroxide, magnesium peroxide, sodium metasilicate, and ammonium chloride;
   at least a powdery carrier material selected from the group consisting of alkaline silicate, silicon dioxide, alkaline stearate, and alkaline carbonate; and
   0.5% to 2% by weight of oil; wherein:
   the bleaching composition is in a form of agglomerated particles that are free-flowing and dust free.

2. The bleaching composition of claim 1, wherein the agglomerated particles are retainable on a 300 mesh sieve.

3. The bleaching composition of claim 1, wherein the powder ingredient is present by weight from 25% to 65%.

4. The bleaching composition of claim 1, wherein the oil is inert with respect to the other ingredients of the bleaching composition, and is selected from the group consisting of mineral oil, silicone oil, hydrocarbons with ether linkages, hydrocarbon with polyethylene glycol chains, animal oil and vegetable oil.

5. The bleaching composition of claim 1, wherein the oil has a viscosity in the range of 5 $mm^2/s$ to 350 $mm^2/s$.

6. A bleaching composition consisting of:
   at least a powder ingredient that is capable of retaining oil on its surface selected from the group consisting of potassium persulfate, ammonium persulfate, sodium persulfate, urea peroxide, melamine peroxide, strontium peroxide, magnesium peroxide, sodium metasilicate, and ammonium chloride;
   at least a powdery carrier material selected from the group consisting of alkaline silicate, silicon dioxide, alkaline stearate, and alkaline carbonate; and
   0.5% to 2% by weight of oil; wherein:
   the bleaching composition is in a form of agglomerated particles that are retainable on a 300 mesh sieve; and the powder ingredient is present by weight from 25% to 65%.

7. The bleaching composition of claim 6, wherein the oil is present by weight from 1% to 2%.

8. The bleaching composition of claim 6, wherein the powder ingredient is present by weight from 35% to 50%.

9. The bleaching composition of claim 6, wherein the oil is mineral oil or silicone oil with a viscosity in the range of 7 $mm^2/s$ to 120 $mm^2/s$.

* * * * *